(12) United States Patent
Vepari et al.

(10) Patent No.: US 9,290,579 B2
(45) Date of Patent: Mar. 22, 2016

(54) COVALENTLY IMMOBILIZED PROTEIN GRADIENTS IN THREE-DIMENSIONAL POROUS SCAFFOLDS

(75) Inventors: Charu Vepari, Waltham, MA (US); David L. Kaplan, Concord, MA (US); Gordana Vunjak-Novakovic, New York, NY (US)

(73) Assignees: Trustees of Tufts College, Medford, MA (US); Massachusetts Institute of Technology, Cambridge, MA (US)

( * ) Notice: Subject to any disclaimer, the term of this patent is extended or adjusted under 35 U.S.C. 154(b) by 1247 days.

(21) Appl. No.: 11/407,373

(22) Filed: Apr. 19, 2006

(65) Prior Publication Data

US 2007/0212730 A1 Sep. 13, 2007

Related U.S. Application Data

(60) Provisional application No. 60/673,074, filed on Apr. 20, 2005.

(51) Int. Cl.
| | | |
|---|---|---|
| C07K 17/02 | (2006.01) | |
| C12N 11/02 | (2006.01) | |
| C07K 17/04 | (2006.01) | |
| C12N 11/04 | (2006.01) | |
| C12N 11/06 | (2006.01) | |
| C12N 11/10 | (2006.01) | |

(52) U.S. Cl.
CPC ............... *C07K 17/02* (2013.01); *C07K 17/04* (2013.01); *C12N 11/02* (2013.01); *C12N 11/04* (2013.01); *C12N 11/06* (2013.01); *C12N 11/10* (2013.01)

(58) Field of Classification Search
None
See application file for complete search history.

(56) References Cited

U.S. PATENT DOCUMENTS

| | | | | |
|---|---|---|---|---|
| 5,736,188 A | * | 4/1998 | Alcock et al. ................. | 427/2.11 |
| 2003/0100846 A1 | * | 5/2003 | Custer et al. ................... | 600/573 |
| 2004/0005363 A1 | * | 1/2004 | Tsukada et al. ............... | 424/537 |
| 2004/0028655 A1 | * | 2/2004 | Nelson et al. ................. | 424/93.2 |
| 2006/0251719 A1 | * | 11/2006 | Tabata ........................... | 424/468 |
| 2006/0273279 A1 | * | 12/2006 | Kaplan et al. ..................... | 252/1 |

FOREIGN PATENT DOCUMENTS

WO  WO 2004/062697 A2  7/2004

OTHER PUBLICATIONS

Tsukada et al. (1994) Preparation and Application of Porous Silk Fibroin Materials. Journal of Applied Polymer Science, vol. 54, pp. 507-514.*

Li et al. (2002) Study on Porous Fibroin Materials:3. Influence of Repeated Freeze-Thawing on the Structure and Properties of Porous Silk Fibroin Materials, Polymer Adv. Technology, vol. 13, pp. 605-610.*

Elçin et al. (1996) Controlled release of endothelial cell growth factor from chitosan-albumin microspheres for localized angiogenesis: in vitro and in vivo studies. Artificial Cells Blood Substitutes and Immobilization Biotechnology May 1996; vol. 24 No. 3, pp. 257-271.*

Vassilis Karageorgiou et al., "Bone morphogenetic protein-2 decorated silk fibroin films induce osteogenic differentiation of human bone marrow stromal cells" pp. 528-537, 2004 Wiley Periodicals, Inc.

Rina Nazarov et al., "Porous 3-D Scaffolds from Regenerated Silk Fibroin", pp. 718-726, American Chemical Society, 2004.

Si-Nae Park et all., "Biological characterization of EDC-cross-linked collagen-hyaluronic acid matrix in dermal tissue restoration" pp. 1631-1641, Elsevier Science Ltd, 2002 All Rights Reserved.

Tai Hyun Park and Michael L. Shuler, "Review: Integration of Cell Culture and Microfabrication Technology", pp. 243-253, American Chemical Society and Americal Institute of Chemical Engineers, 2003.

Francisco Rojas-Melgarejo et al., "Immobilization of horseradish peroxidase on cinnamic carbohydrate esters" pp. 1455-1464, Elsevier Ltd., All Rights Reserved 2003.

Susan Sofia et al., "Functionalized silk-based biomaterials for bone formation", Journal of Biomedical Materials Research, vol. 54, pp. 139-148, 2000.

Noo Li Jeon et al., "Neutrophil chemotaxis in linear and complex gradients of interleukin-8 formed in a microfabricated device" pp. 826-830, 2002.

J.S. Pieper et al., "Development of tailor-made collagen-glycosaminoglycan matrices: EDC/NHS crosslinking, and ultrastructural aspects", pp. 581-593, Elsevier Science Ltd 2000.

Todd C. McDevitt et al., "Spatially organized layers of cardiomyocytes on biodegradable polyurethane films for myocardial repair" pp. 586-595, Wiley Periodicals, Inc. 2003.

Daniel T. Chiu et al., "Patterned deposition of cells and proteins onto surfaces by using three-dimensional microfluidic systems" pp. 2408-2413, Mar. 14, 2000.

Demura, et al., "Immobilization of Biocatalysts with Bombyx mori Silk Fibroin by Several Kinds of Physical Treatment and Its Application to Glucose Sensors," Biosensors. vol. 4, pp. 361-372 (1989).

* cited by examiner

*Primary Examiner* — Lisa J Hobbs
(74) *Attorney, Agent, or Firm* — Choate, Hall & Stewart, LLP; Brian E. Reese

(57) ABSTRACT

The invention provides a method for forming an immobilized agent gradient within a 3-dimensional porous scaffold. A 3-dimensional scaffold formed from a biocompatible material is provided. The surface of the scaffold and/or the agent is activated so as to allow binding of the agent to the scaffold. The activated scaffold is contacted with a solution containing the agent. Contact with the solution is maintained for a sufficient period of time to allow diffusion of the solution through a portion of the scaffold, thereby forming a desired gradient of the agent through the 3-dimensional scaffold.

41 Claims, 11 Drawing Sheets

2A

2B

3A

3B

6A

6B

9A

9B

10A

10B

COVALENTLY IMMOBILIZED PROTEIN GRADIENTS IN THREE-DIMENSIONAL POROUS SCAFFOLDS

CROSS-REFERENCE TO RELATED APPLICATIONS

This application claims the benefit under 35 U.S.C. §119 (e) of the U.S. Provisional Application Ser. No. 60/673,074, filed on Apr. 20, 2005, the entire contents of which are incorporated herein by reference.

GOVERNMENT SUPPORT

This invention was made with government support under grant number P41 EB002520 awarded by the National Institutes of Health. The government has certain rights in this invention.

BACKGROUND OF THE INVENTION

Immobilized enzymes are utilized extensively in biosensor and related detection protocols in many technological applications. Immobilization generally offers improved enzyme stability and localization in comparison to soluble forms (Rojas-Melgarejo 2003). 1-Ethyl-3-(3-dimethylaminopropyl)-carbodiimide (EDC) is the most common coupling chemistry used to couple proteins to many biomaterials. For example, to couple BMP-2 onto silk fibroin (Karageorgiou et al. 2004), to crosslink collagen and hyaluronic acid (Park et al. 2003) and collagen with glycosaminoglycan (Pieper et al. 2000). Covalent coupling of enzymes is necessary for gradient formation in order to further improve control of enzyme location and stability in comparison to more homogenous distributions currently studied. In particular, needs related to multidetection biosensor formats and gradients in responses and functions of such material would potentially advance technological utility of these materials.

To control protein patterning on surfaces there are several methods available. The most well-known is soft lithography (using PDMS as the material) such as microcontact printing (μCP) and micromolding in capillaries (MIMC). μCP is a method where a two-dimensional stamp creates complex patterns of proteins or biological materials (usually) on PDMS slabs. Using μCP, one substance can be printed at a time into complex shapes or self-assembled monolayers (Chiu et al. 2000) Park and Shuler 2003). μCP has also been used for tissue engineering applications. For example, laminin lanes were printed on biodegradable polyurethane, seeded with cardiomyocytes which grew to two-three cells layers thick in an attempt to create engineered tissue (McDevitt et al. 2003). MIMIC is another soft lithographic technique which uses microchannels formed by contacting the PDMS structure with a substrate. Desired fluid is flown to certain areas to form patterns (Park and Shuler 2003). The disadvantage of the two-dimensional flow through microchannels is that it is restricted to simple patterns. An extension of this method is a three-dimensional microfluidic channel system whereby complex and discontinuous patterns can be generated using more than one substance at a given time on a planar surface (Chiu et al. 2000). It would be interesting and useful if this method could be extended to create micro-patterned protein solutions in three-dimensional gels and foams. Nanoscale techniques, such as dip pen nanolithography, have also been used to pattern proteins such as collagen (Wilson et al., 2001). However, the scale and speed of such processes are limiting and the process is confined to two dimensional surfaces.

Current methods to develop protein gradients on surfaces are derived from the field of chemotaxis. The study of chemotaxis was accelerated by formation of non-linear gradients of soluble growth factors generated in the Boyden Chamber. However, the gradients generated were unstable and hence could not be used for a longer period of time (Boyden 1962). A microfluidic gradient generator was developed by Li Jeon et al. (2002) to make stable (stable until flow of is maintained), soluble and complex gradients of interleukin-8. However smearing of the gradient was observed and since the gradient was developed on two-dimensional PDMS slabs, it can only be extended to use in vitro and for shorter periods of time (Li Jeon et al. 2002). Accordingly, there is a need to develop 3D controlled immobilized protein gradient materials.

SUMMARY OF THE INVENTION

The invention provides a method for forming an immobilized agent gradient within a 3-dimensional porous scaffold. A 3-dimensional scaffold formed from a biocompatible material is provided. The surface of the scaffold is activated so as to allow binding of the agent. The activated scaffold is contacted with a solution containing the agent. Alternatively, the agent is activated and then contacted with the scaffold. Alternatively, both the agent and the scaffold are activated prior to contact with each other. Contact with the solution is maintained for a sufficient period of time to allow diffusion of the solution through a portion of the scaffold, thereby forming a gradient of the protein through the 3-dimensional scaffold.

The solution may be drawn through the scaffold by diffusion. The solution may be drawn through the scaffold by convection, including convection coupled with diffusion.

The biocompatible material forming the 3-dimensional scaffold may be silk, collagen, keratin, fibronectin, chitosan, hyaluronic acid or an alginate. The biocompatible material forming the 3-dimensional scaffold may be a biocompatible polymer such as polylactic acid (PLA), polyglycolic acid (PGA), a combination of biocompatible polymers. In one embodiment, the biocompatible material is not a biocompatible polymer.

Multiple gradients may be formed in the scaffold. The gradients may be in different directions in the scaffold. The multiple gradients may each comprise different immobilized agents.

The immobilized agent in the scaffold may be a protein such as an enzyme, a cytokines, a growth factor, a cell binding domain and/or other cell signaling factor. The immobilized agent may be a chemotactic agent such as ascorbic acid, dexamethasone, retinoic acid. The immobilized agent may be a nucleic acid.

One preferred agent for activating the scaffold is 1-ethyl-3-(3-dimethylaminopropyl)-carbodiimide (EDC).

BRIEF DESCRIPTION OF THE DRAWINGS

FIG. 7A shows a droplet of HRP solution (illustrated as a black spot) activated with coupling agent at a desired volume is placed underneath the scaffold. Scaffold Dimensions: 12 (length)×3.5 (breadth)×2.5 (height) mm$^3$. FIG. 7B shows the HRP solution was allowed to diffuse (Diffusion method) through the scaffold. FIG. 7C shows Sections used in analysis—Dimensions: 2 (length)×3.5 (breadth)×2.5 (height) mm$^3$.

FIG. 8A shows a droplet of HRP solution (illustrated as a black spot) activated with coupling agent in a desired volume is placed underneath the scaffold. Dimensions: 12 (length)×3.5 (breadth)×2.5 height) mm$^3$. FIG. 8B shows a pipette placed above the scaffold creates convection within the scaffold to form a gradient. FIG. 8C shows sections used in analysis—Dimensions: 2 (length)×3.5 (breadth)×2.5 (height) mm$^3$.

DETAILED DESCRIPTION OF THE INVENTION

Figure 1:
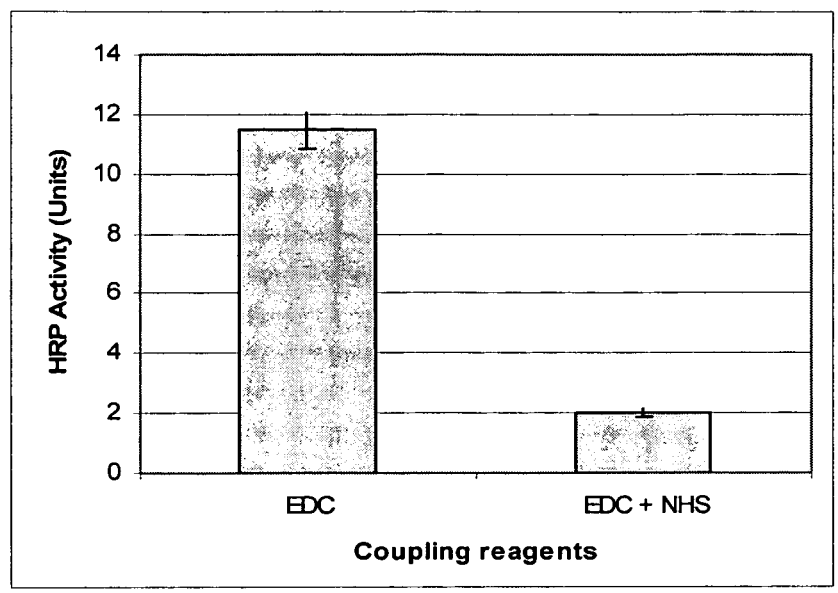
FIG. 1 shows comparison of activity between coupled HRP using EDC versus coupled HRP using EDC+NHS (molar ratio of EDC:NHS used 2.3). N=4-6. The difference between the activities was found significant by t-test, p<0.001

The present invention provides a method to form covalently immobilized gradients of labile agents in 3D porous scaffold systems. Proteins may be immobilized in the scaffold. Chemotactic agents may also be immobilized in the scaffold. The method is demonstrated with both an enzyme, horseradish Peroxidase (HRP), and a cytokine, rhBMP-2. Gradients were formed within silk fibroin 3D scaffolds. In one example, a covalently immobilized rhBMP-2 gradient was made. After seeding with bone marrow stromal cells, a gradient response of mineral calcium was observed demonstrating a functional tissue outcome with the cytokine. The method of the present invention is advantageous in that it does not need any special equipment and can be manufactured at the bench using a pipette.

The method of the present invention can also be translated to developing gradients from two ends of a scaffold, which can be useful for applications in tissue engineering—such as the formation of gradients or interfaces among two different tissue types. Hence two different agents can be immobilized with increasing concentrations of gradients moving towards opposite ends, such as for osteochondral plugs, ligament/bone interfaces and similar needs.

In one embodiment, the present invention provides a method for forming an immobilized agent gradient within a 3-dimensional porous scaffold. The method comprises: (a) providing a 3-dimensional scaffold formed from a biocompatible material; (b) activating the surface of said scaffold and/or activating the agent to allow binding of the agent and the scaffold; (c) contacting the scaffold with a solution containing the agent for a sufficient period of time to allow diffusion of the solution through a portion of the scaffold, whereby a gradient is formed.

In one embodiment, the solution is drawn through the scaffold using, for example, a pipette. In one embodiment, the solution is drawn through the scaffold using a mechanized pipette or automated pipette. In such an embodiment, the velocity by which the solution is drawn through the scaffold is approximately reproducible. The gradient formed may be may be varied and is controlled by changing the volume or concentration of the solution of the agent to be immobilized or by changing the velocity by which the solution is drawn through the scaffold. Biocompatible materials useful in forming the scaffold include any protein having acid or amine groups present, including, for example, silk, collagen, keratin, fibronectin, elastins and related structural proteins. In addition, other biopolymers with similar functional groups, such as chitosan, hyaluronic acid, alginates and others. Alternatively, biocompatible polymer materials may be used for the scaffold, for example, polylactic acid (PLA), polyglycolic acid (PGA), hydrogels and others.

Proteins and peptides can be bound to the scaffold including, for example, enzymes, cytokines, growth factors, cell binding domains and other cell signaling factors. Alternatively, chemotactic agents can be bound to the scaffold, including, for example, ascorbic acid, dexamethasone, retinoic acid. Alternatively, nucleic acids may be bound to the scaffold. In one embodiment, the immobilized agent is not a non-protein. Alternatively, more than one type of protein, chemotactic agent or combination thereof may be bound to the scaffold.

The term "activation" or "activating" means modification of the scaffold surface (e.g., a functional group on the surface) to enable coupling a target protein thereto.

Activating agents that may be used for the purposes of the present invention are per se well known to a person skilled in the art and may readily be selected for each particular situation.

The choice of activating agent (and method) depends, of course, on the functional group to be activated and on the desired reactive group to be obtained by the activation, which in turn depends on the binding agent to be coupled to the substrate surface. Exemplary functional group/activating agent combinations include those introducing hydroxysuccinimide esters, nitro- and dinitrophenyl esters, tosylates, mesylates, triflates and disulfides. For example, a hydroxyl group may be reacted to activated ester with disuccinic carbonate, or to epoxide with a diepoxide. A carboxy group may be activated to N-hydroxysuccinimide ester by reaction with N 20 hydroxysuccinimide (NHS) and carbodiimide, e.g., EDC, or to dinitrophenyl ester by reaction with dinitrophenol. A thiol (mercapto) group may be activated to a disulfide group by reaction with e.g. a i dipyridyldisulfide or (2-pyridnyldithio)ethaneamine.

Gradients of growth factors in embryonic development guide cells into developing tissues and in determining the boundary of the tissues. It is hypothesized that similar factor gradients are also responsible for regeneration in the adult. Bone and cartilage regeneration, nerve growth, and angiogenesis all have a growth factor gradient component.

The gradient method developed is fundamental to use in tissue engineering. It can be used as a model to study regeneration and repair or be used for therapeutic purposes.

Using diffusion/immobilization of enzymes or growth factors into porous scaffolds to make immobilized gradients should provide new options for designer features in biomaterial scaffolds to offer improved control of cell and tissue outcomes in vitro and in vivo. This control will include new aspects of regional patterned on gradient outcomes.

Methods useful for preparation of aqueous silk fibroin solutions are disclosed in WO 2005/012606. Methods useful for forming silk fibroin scaffolds are set forth in WO 2004/000915, WO 2004/001103, WO 2004/062697.

EXAMPLE 1

Materials and Methods

Preparation of Silk Fibroin Scaffold

Cocoons from Bombyx mori (supplied by M. Tsukada, Institute of Sericulture, Tsukuda, Japan) were de-gummed for 1 hr in 0.02 M $Na_2CO_3$ (Fisher, Pittsburgh, Pa.) solution to extract sericin from fibroin. Silk fibroin was washed thoroughly to remove sericin, dried and dissolved in 9.3 M lithium bromide at 500 c to generate a 10% (w/v) solution. The solution was dialyzed in a Slide-A-Lyzer (3500 MW cassette, Pierce, Ill.) against water for 3 days to remove lithium bromide. The solution was lyophilized and then dissolved in hexafluoro-2-propanol (Aldrich, Milwaukee, Wis.) to generate a 15% silk solution, a modification of our previously reported procedure [(Nazarov et al. 2004; Sofia et al. 2001).

Granular sodium chloride (crystal sizes from 150 to 700 µm, Sigma, Mo.) was used as a porogen (Nazarov et al, 2004). The 15% silk solution was poured into a Teflon hexagon dish (medium size, Fisher, Pittsburgh, Pa.) containing leveled sodium chloride. The dish was covered with a parafilm wax sheet and left at 4° C. for 30 minutes to allow the fibroin solution to diffuse around the salt crystals. The weight ratio of salt to fibroin used was 21 to 1. After evaporation of the hexafluoro-2-propanol for 24 hours, the salt/silk composite was immersed in methanol (Fisher, Pittsburgh, Pa.) for at least 30 minutes to induce the β-sheet structural transition, ensuring the scaffolds would be insoluble in aqueous solutions. After the methanol was removed, the scaffolds were immersed in water several times for at least a day to extract residual salt. The scaffold was removed and cut to 12 (length)×3.5 (breadth)×2.5 (height) $mm^3$ dimensions. Scaffold size was kept constant throughout the gradient experiments. The volume of the scaffold was determined to be 0.105 $cm^3$ from scaffold dimensions. Experimentally, the void volume (0.075 ul) was determined by measuring the liquid extruded with a pipette from a fully hydrated scaffold.

FIG. 13 is a schematic showing of the preparation of silk fibroin scaffolds.

Coupling of Horseradish Peroxidase (HRP)

HRP (Type VI-A, EC 1.11.1.7, Sigma, Mo.) was used without any further purification for immobilization on silk fibroin scaffolds using 1-ethyl-3-(3-dimethylaminopropyl carbodiimide (EDC) (Pierce Chemicals, Ill.) chemistry using a modification of our previously reported procedure (Sofia et al. 2001). HRP solutions (0.2 mg/mL, 0.5 mg/mL and 1 mg/mL) were used to form different gradient slopes. Various concentrations of EDC (from 1000 to 10000 mg of EDC/per mg of HRP) were used to determine the best EDC/HRP ratio. EDC was dissolved in the HRP solution and then immediately applied to the fibroin scaffolds (method described in section describing Immobilized HRP gradients). Reactions proceeded from 15 to 60 minutes. NHS (N-hydroxysuccinimide) (Pierce, Ill.) was used with EDC in the molar ratio of 2.3 to 1. A 0.1 M 2-(N-morpholino) ethanesulfonic acid (MES) solution) (Pierce Chemicals, Ill.) with 0.9% sodium chloride (pH 5.6) was used as the reaction buffer. The pH of the reaction buffer was chosen to minimize HRP non-specific adsorption on the protein scaffolds (described in results section). After completion of reactions, all scaffolds were washed five times with the reaction buffer, followed by two times with $dH_2O$.

Measurement of HRP Activity

A 3,3'5,5' Tetramethylbenzidine (TMB) solution (BioFX Labs, Mo.) was used to detect HRP activity. TMB solution was directly added to the pieces of scaffold and the formation of one electron oxidation product (blue color) was stopped by the addition of an equal volume of 0.1M sulfuric acid to form the two electron oxidation product (yellow color) after one minute. Formation of the yellow product was detected at 450 nm. Using an extinction coefficient of $5.9 \times 10^4$ $M^{-1}$ $cm^{-1}$ (Josephy 1982), the activity of immobilized enzyme was calculated. One unit of HRP activity was defined as the amount of enzyme required to oxidize 1 Mm of product in 1 minute at room temperature in 1 mL of reaction media at pH 5.6.

Immobilized HRP Gradients

Scaffolds were soaked in reaction-buffer for 30 minutes and held in a vertical position. A drop of HRP solution with EDC dissolved was placed below the scaffold (concentration and volume of HRP solution were changed according to experiment). The gradient was allowed to develop by diffusion (Scheme 1) or convection coupled with diffusion (Scheme 2). With the diffusion method, the scaffold was placed over the HRP droplet and diffusion was allowed to occur for 15 minutes. With the convection method (coupled with diffusion), the scaffold was placed over the HRP droplet while a measured amount of liquid was drawn upwards through the scaffold using a pipette (velocity of liquid drawn up was experimentally estimated to be from 0.3 to 1.2 mL/min). After completion of the reaction, scaffolds were transferred to Eppendorf tubes and washed five times with reaction buffer followed by two times with $dH_2O$. Eppendorf tubes were changed between washes to avoid re-adsorption of protein from the eppendorf tubes. After the washing, the scaffolds (12 mm in length) were cut into six pieces, each with the dimensions of 2 mm×3.5 mm×2.5 mm. Each piece was placed in an Eppendorf tube and allowed to react with the TMB solution (BioFX Labs, Mo.). Reactions ran for one minute before the addition of equal volume of 0.1M sulfuric acid. The supernatant was read at 450 nm and the HRP activity was determined.

Statistical Analysis

Student t-test (two-sample equal variances) was used to compare and evaluate means between data groups. For this test, p values less than 0.05 were considered significant unless specified.

Results

HRP Immobilization using Carbodiimide Chemistry

EDC was used to immobilize HRP to silk fibroin scaffolds. To reduce the amount of cross-linking between HRP molecules, N-hydroxysuccinimide (NHS) is usually added to stabilize the amine reactive intermediate formed, thereby increasing the yield of conjugation (Hermanson 1996). However, activation of HRP by EDC in conjunction with NHS, resulted only in 18% of the activity observed when compared to activation of HRP by EDC alone (FIG. 1). Manipulating EDC concentration and pH of the reaction buffer can also produce differences in immobilization yields (Olde Damink et al. 1996). Another strategy to increase yield of immobilized HRP on silk scaffolds, is to either increase coupling sites on the silk scaffold or increase the concentration of HRP solution employed.

Figure 2:
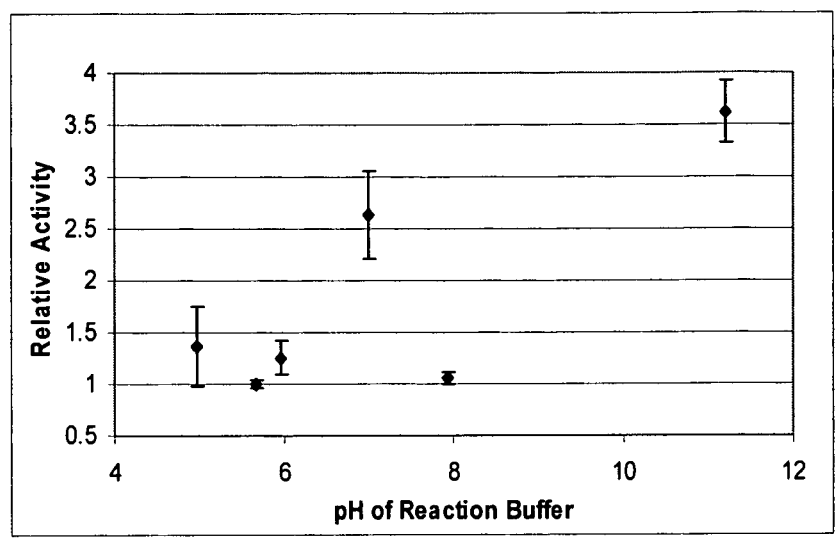
FIG. 2A shows relative activities of HRP adsorbed to silk scaffolds with increasing pH of reaction buffer (0.1 M MES, 0.9% NaCl). N=3. Relative activity was calculated by dividing activities of all pHs to the activity of the reaction buffer pH with the lowest activity.
FIG. 2B shows optimum ratio of EDC to HRP (mg/mg) coupled with silk fibroin scaffold, determined by measuring HRP activity. N=3. Highest activity was obtained at 7500 mg of EDC per mg of HRP.
Figure 2:
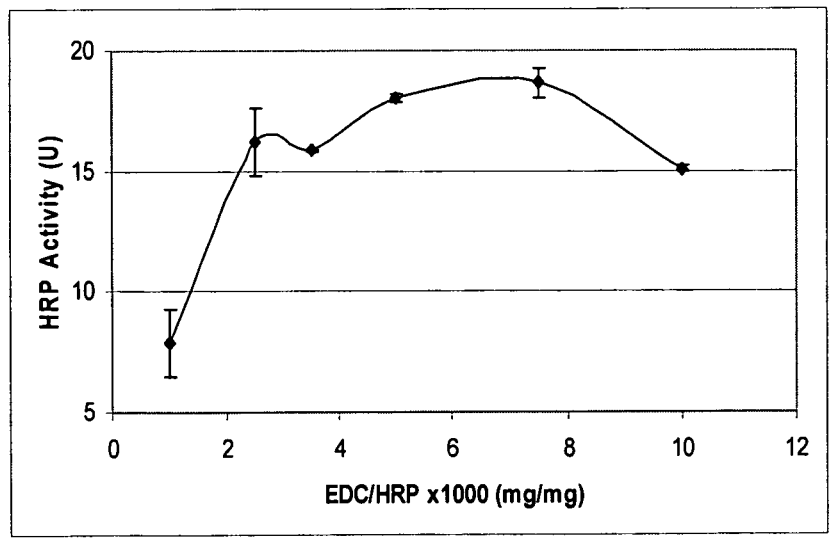

EDC is active from pH 4.5 to 7.5 which is an optimum pH for the stability of several proteins. The isourea byproduct formed during this reaction is water soluble and hence easily removed, leaving the scaffold free of any cross-linking products (Hermanson 1996; Olde Damink et al. 1996). To accurately detect the amount of covalently coupled HRP, with the least possible error arising from HRP being adsorbed to the scaffold during the reaction, a reaction pH was selected where HRP adsorption was lowest. FIG. 2A shows the relative activity of HRP adsorbed to scaffolds at different pH levels compared to the lowest amount of HRP adsorbed at pH 5.6. The pH levels found to have the lowest adsorption were pH 5.6 and pH 8 as measured by TMB oxidation. Since EDC is active at an optimum pH of 4.7 to 6 (Hermanson 1996), a pH of 5.6 was chosen for the reaction buffer and all reactions were carried out at this pH to minimize nonspecific adsorption while maintaining coupling reactivity. The pH adsorption profile was not due to the activity of TMB at different pH levels since all scaffolds were washed extensively with water before the addition of TMB. It should be noted that the silk fibroin protein scaffolds are stable under these conditions.

The major isoenzyme of HRP of type VIA has a Pi of 9.0 and the next most common isozyme has a Pi around 7.0. At both these pH levels, an increase in activity was found, suggesting precipitation of the above mentioned isoenzymes of HRP on silk fibroin scaffolds, hence an increase in HRP activity at those pH levels. HRP protein adsorbed on silk fibroin scaffolds resulted in 2.55 (±0.18) units of HRP activity detected on the entire scaffold when exposed to 0.002 mg of HRP using a reaction buffer of pH 5.6. HRP activity from adsorption accounts for only 6% of HRP activity detected by coupling to entire silk scaffolds in similar conditions.

The optimal ratio of HRP to EDC was determined by increasing the concentration of EDC to a fixed concentration of HRP solution. The optimal ratio was 7500 mg of EDC per mg of HRP coupled to the silk fibroin scaffolds (FIG. 2B). This ratio was used in immobilization of HRP within silk scaffolds in a gradient fashion. A further increase in EDC concentration decreased activity of coupled HRP, either due to precipitation of HRP (Hermanson 1996; Puleo et al. 2002) or due to HRP-HRP coupling. Increases in EDC concentration have inactivated other proteins like $\beta$-glucosidase when one mole of EDC was added to one mole of $\beta$-glucosidase (Rashid and Siddiqui 1998).

Immobilized HRP Gradients

HRP was covalently immobilized, using EDC chemistry, on three-dimensional fibroin scaffolds in a gradient format. Several parameters can be controlled to create gradients with the experimental system described. Two parameters were assessed, allowing various volume of the droplet to diffuse through the scaffold: the 'diffusion method' and the 'convection method'. The convection method is where a volume of liquid is pulled up through the scaffold (convection) and keeping the volume of HRP solution constant. In the convection method, it is speculated that gradient formation is primarily through convection, however there are some effects of diffusion coupled with convection.

Figure 3:
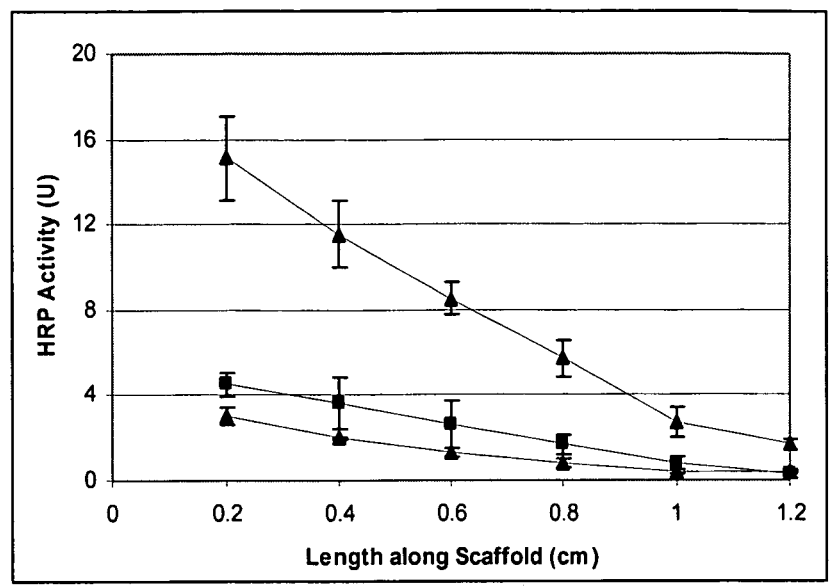
FIG. 3A shows diffusion of HRP (0.2 mg/mL) with 0.010 (-▲-), 0.005 (-■-) and 0.0025 (-●-) mL of HRP solution. N=3. Difference in the slopes of HRP activity with 0.010 (-▲-), 0.005 (-■-) and 0.0025 (-●-) mL is observed. Statistical difference in HRP activity found between diffusion with 0.010 mL of HRP solution compared to diffusion of 0.005 and 0.0025 mL of HRP solution along the entire length of the scaffold.
FIG. 3B shows diffusion of HRP activity with 0.005 mL of 1 mg/mL (-■-), 0.5 mg/mL (-●-) and 0.2 mg/mL (-▲-) of HRP solution. N=3-8. Slopes of the gradients are similar. Significant statistical difference in HRP activity between diffusion of 0.2 mg/mL HRP solution versus 0.5 mg/mL and 1 mg/mL HRP solution.
Figure 3:
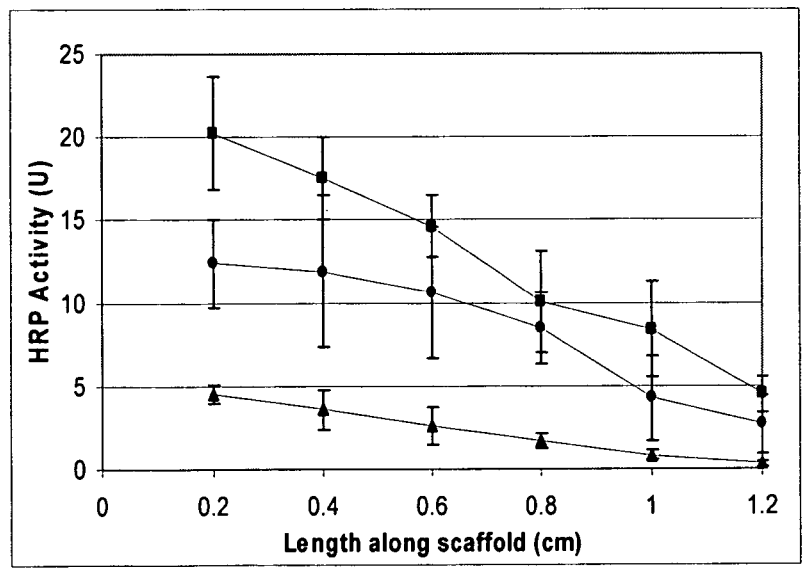

Using the diffusion method, the volume of the activated HRP solution (10, 5 and 2.5 ul) was changed to form immobilized HRP gradients of different slopes within the scaffold. FIG. 3A shows increasing slopes of immobilized HRP gradients with the addition of the activated HRP solution. Different quantities of total HRP to each scaffold was brought about by changing the volume of the activated HRP solution, keeping the concentration of the starting HRP solution droplet constant. The results are reported on the y-axis against the length of the scaffold (1.2 cm). A statistical difference in HRP activity was found between the 10 ul diffusion gradient and the 5 ul and 2.5 ul diffusion gradient at all points. There is a statistical difference in HRP activity between 5 ul and 2.5 ul diffusion gradients at the farthest end from the HRP solution origin. It is demonstrated in the diffusion method that the outcome of the gradient is controlled by changing the volume of the HRP solution. However, the gradients could also be generated by controlling the concentration of immobilization sites (a reverse gradient) on the scaffold.

Gradients by the diffusion method were also produced by varying the concentration of activated HRP (FIG. 3B). Immobilized gradients were made by diffusion of 5 Ml activated HRP solution of varying concentrations. The gradients generated by diffusion 0.2 mg/mL, 0.5 mg/mL, and 1 mg/mL HRP solutions have similar slopes and show significant statistical differences in HRP activity.

Figure 4:
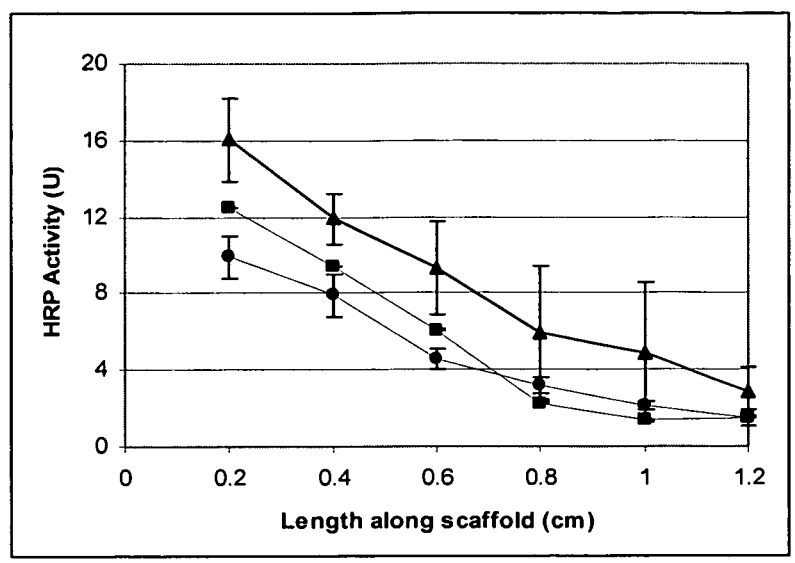
FIG. 4 shows HRP gradient on silk scaffold with constant volume of HRP drop and 0.030 mL (-▲-), 0.010 mL (-■-) and 0.005 mL (-●-) as convection volumes pipetted from the top of the scaffold. N=3. Data points at 2 mm length on the scaffold were found significant among the three volumes.

Using the convection method, which is coupled to some degree with diffusion, the volume of the activated HRP solution was kept constant changing the volume of liquid pulled (FIG. 4) (30, 10 and 5 μL) through a hydrated scaffold. Convection within the scaffold results in an immobilized HRP gradient pattern. For the varying volumes of liquid pulled, there no difference in gradient slopes. Further, difference in HRP activity among the gradient slopes made by the convection method were found significant only at the end of the scaffold furthest from the HRP solution droplet. It is speculated that since the convection was created by a pipette, changes in velocity could be responsible for the increased variance.

Figure 5:
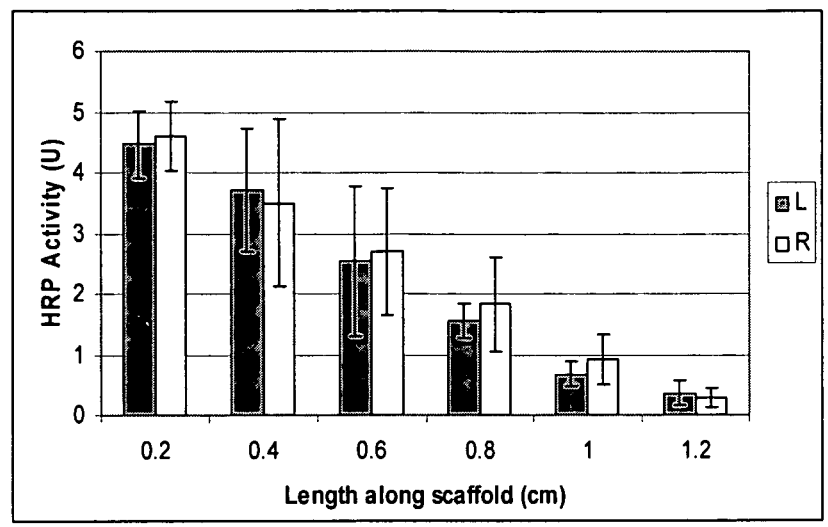
FIG. 5 shows immobilized HRP gradient using diffusion of 0.005 mL of HRP solution. Activity of scaffolds cut in both x-axis (length along scaffold) and in the z-axis (long axis) is shown. Symmetry between left (L) and right (R) hand side (z-axis) of the scaffold is shown. N=3. No statistical difference was found between L and R at any point on the length along the scaffold (using t-test p<0.1).

Overall, the diffusion method produced more controllable immobilized gradient outcomes compared to the convection method. Further, the diffusion method was simpler than the convection method for coupling HRP within silk scaffolds in gradient patterns. HRP gradients formed were found to be bilaterally symmetric when the 3D scaffolds were cut in half along their long axis. FIG. 5 shows HRP activity of the left (L) and right (R) sides along the 12 mm lengths of the scaffold when cut along the z axis. No statistical difference was found between L and R at any point along the length of the scaffold (using t-test p<0.1) suggesting that gradients formed are uniform along the z axis.

Stability of Immobilized HRP Gradient

Figure 6:
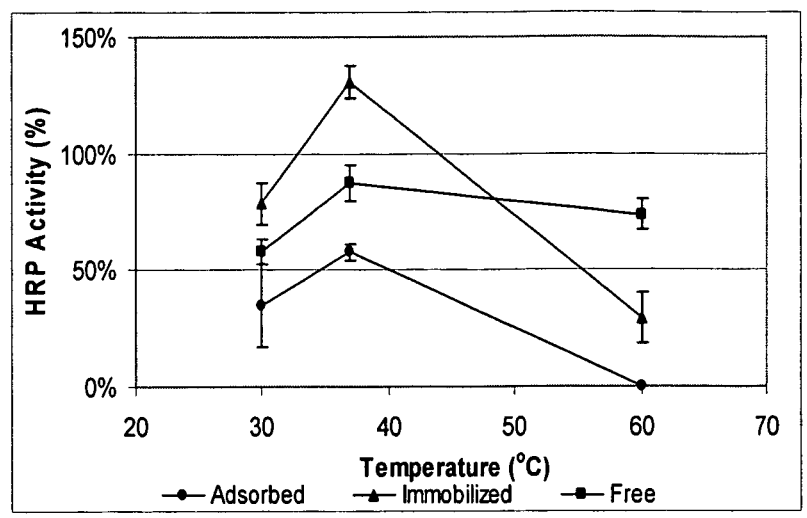
FIG. 6A shows HRP activity (%) for immobilized, adsorbed and free HRP at 30, 37 and 60° C. Scaffolds and free enzyme were incubated at each temperature for 30 min. Percent activity normalized to activity of 25° C. N=4. Difference between immobilized, adsorbed and free HRP at 37° C. and 60° C. was found significant by t-test (p<0.05)
FIG. 6B shows relative Activity (HRP) of immobilized (▲), adsorbed (■) and free (●) HRP as a function of time. Relative activity was calculated as percent from original at time zero.
Figure 6:
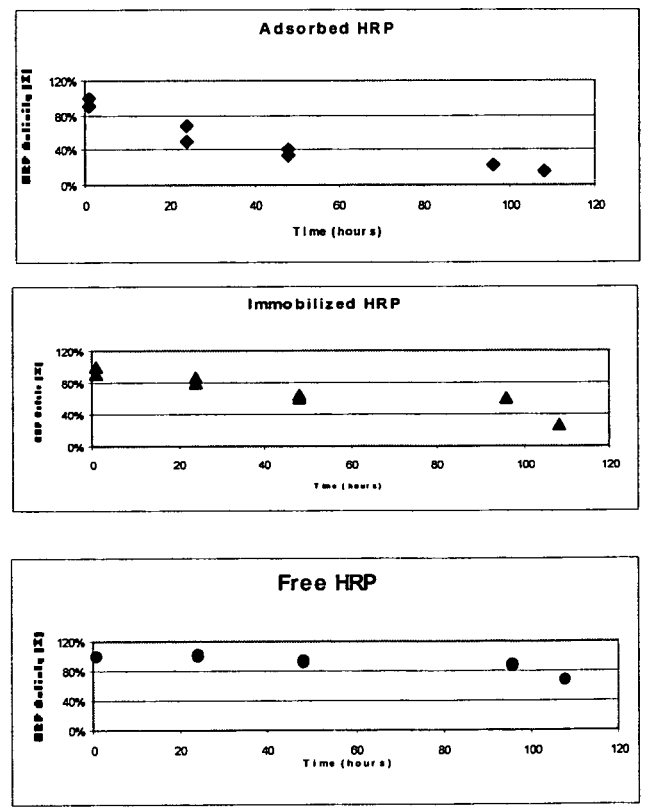
Figure 7:
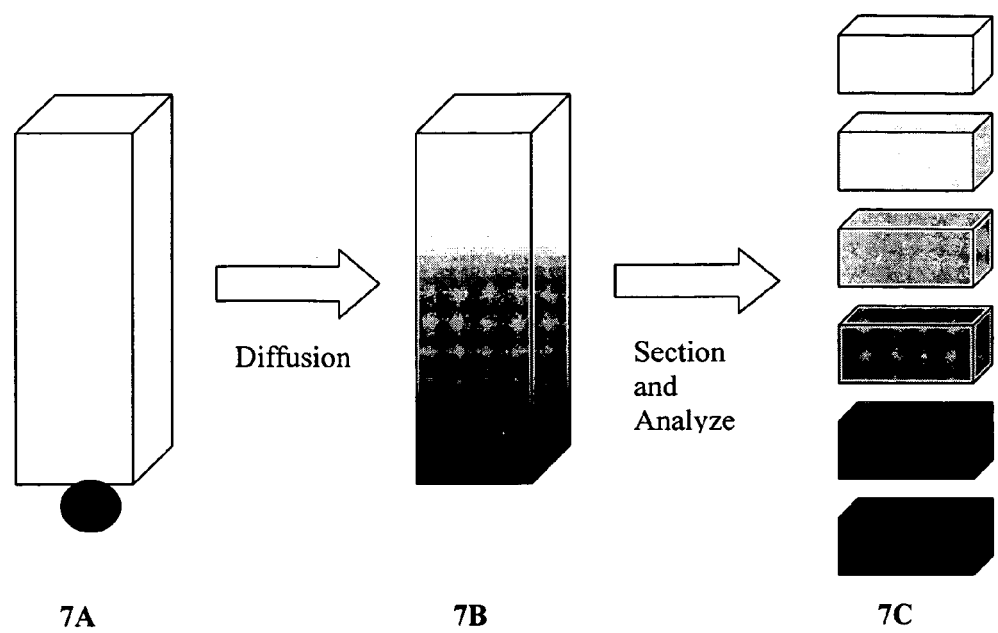
FIG. 7 shows a schematic diagram showing set-up for making protein gradient by diffusion method.
Figure 8:
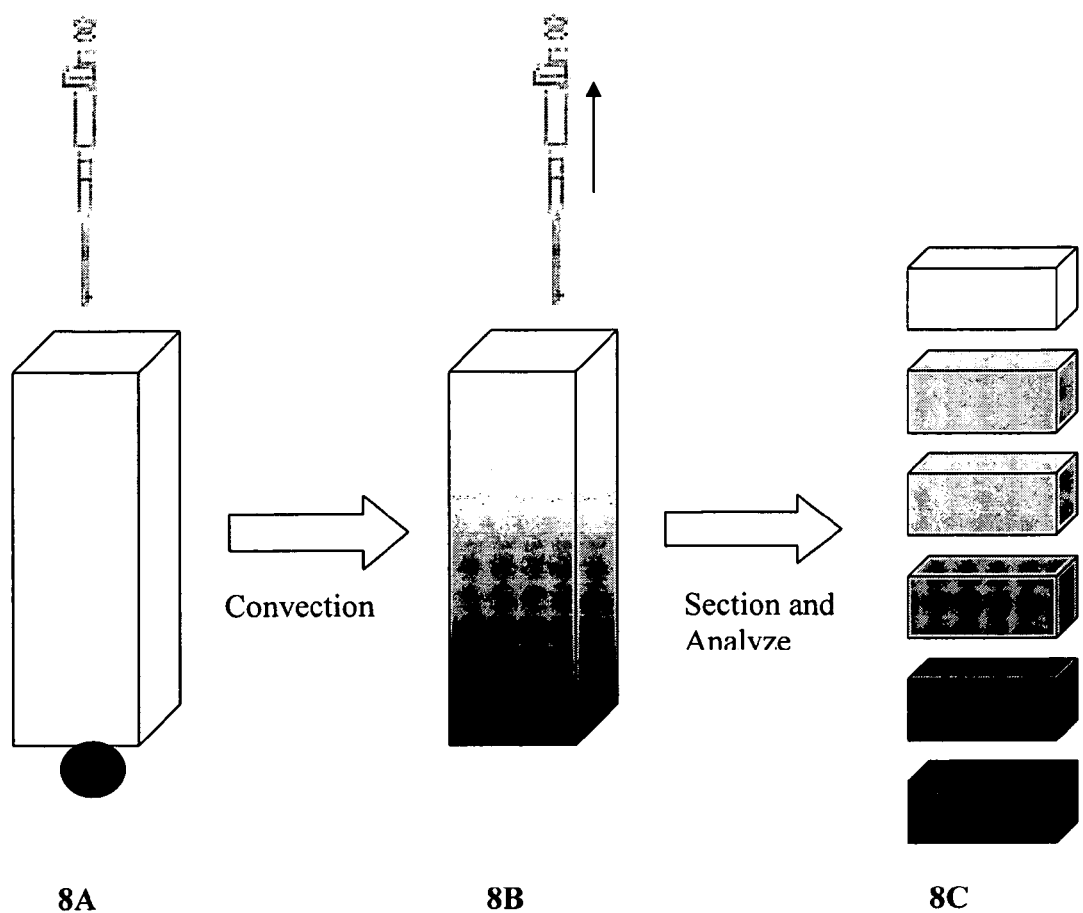
FIG. 8 shows schematic diagram showing set-up for making protein gradient via convection (coupled with diffusion) method.

Stability of covalently coupled, adsorbed and free HRP was compared with respect to time and temperature. Immobilized HRP showed higher activity compared to both adsorbed and free enzyme at 30° C. and 37° C., but activity dropped significantly at 60° C. In all cases, immobilized HRP activity was higher than adsorbed HRP activity (FIG. 6A). The activity of immobilized HRP dropped to 60% of its original activity compared to 90% in free and 20% in adsorbed HRP within 96 hours. Adsorbed protein degraded faster than immobilized protein (FIG. 6B). Surprisingly, free HRP at room temperature had higher activity compared to the immobilized form. The same result (Rojas-Melgarejo 2003) and contradictory results (Chen et al. 2002) have been observed.

To verify if immobilized HRP gradients were stable, a scaffold containing the HRP gradient made by the diffusion method using 5 ul of activated HRP solution was submerged for four days in PBS solution. The gradient pattern was found to be intact, however the slope of the gradient changed from −4.3 (previously measured) to −2.7 (after four days). Change in the slope of gradient may be caused by loss in HRP activity, which was observed in the stability experiments.

Discussion

Diffusion and convection (coupled with diffusion) of activated HRP solution were explored to generate immobilized HRP gradients within 3D silk fibroin scaffolds. The volume and starting concentration of the activated HRP solution were utilized to control the slope and the activity profile of the gradients. The gradients created by this method were mostly linear in profile. Here the HRP was activated by the addition of EDC and subsequent application of the EDC activated HRP solution to the scaffolds. It is also possible to activate the scaffold with EDC first and then add HRP to form covalently coupled HRP gradients which may result in a different gradient profiles with different reaction kinetics.

For diffusion of protein molecules through liquid (this can be assumed because the scaffold is 99% porous) the profile can be predicted by Fick's law of diffusion. Flux, J [$cm^{-2} s^{-1}$], is proportional to the diffusivity $\chi$[$cm^2/s$] and the negative gradient of concentration $\partial C/\partial x$ [$cm^{-3} cm^{-1}$] for different starting conditions of HRP solution. The governing equation for diffusion is, $$J = -\chi \frac{\partial C}{\partial x}$$

However, the gradient outcomes are coupled with reactions which are simultaneously occurring with diffusion: HRP coupling with silk scaffold; HRP-HRP cross-linking; and HRP adsorption to scaffold walls. The latter is the most insignificant, resulting in only about 6% of the total activity observed during covalent coupling of HRP. Rates of the two major reactions, one desired ($k_d$) and one undesired ($k_{ud}$) can be depicted by (assuming first order), $$r_d = -k_d C_{HRP}$$

$$r_{ud} = -k_{ud} C_{HRP}$$

However, rates of reactions which will depend upon the local concentration of HRP, which is constantly changing spatially. We can therefore speculate that rates and orders of reactions also change spatially throughout the scaffold. The diffusion coefficient ($\chi$) can also vary in the scaffold if the diffusion is concentration dependent.

Several aspects of the gradient process can be altered to control outcomes. Gradient formation using the diffusion method changes spatially with time. Therefore, gradient outcomes can be controlled by stopping the reaction at different times resulting in controlling the curvature of the gradient. Fick's second law states that accumulation, dC/dt [$cm^{-3} s^{-1}$], is proportional to the diffusivity $\chi$[$cm^2/s$] and the $2^{nd}$ derivative (or curvature) of the concentration, $\partial^2 C/\partial x^2$ [$cm^{-3} cm^{-2}$]

$$\frac{\partial C}{\partial t} = \chi \frac{\partial^2 C}{\partial x^2}$$

Other parameters that control the formation of gradients are porosity of the gradient (pore size and pore density causing frictional impedance), velocity of volume pulled, surface area of gradient base and degree of scaffold hydration. These parameters were not explored in the current work, but provide options for further control of outcomes. Using these equations, one could model and predict the desirable gradient of several proteins and different reaction conditions.

The immobilized gradient method developed could be useful in several fields. It is a simple method and can be replicated with several other material forms. HRP catalyses several enzymatic reactions, including polymerization reactions (Azevedo 2003). HRP gradients within 3D scaffolds can help in the development of polymer gradients. Since the scaffolds used in this process have a porosity of 99%, significant loading of monomers can be accomplished prior to polymerization. The scaffold could be digested after the reaction, leaving inverse material gradients as the product.

The formation of an immobilized gradient could also be helpful in fundamental studies in understanding enzyme kinetics with effects of diffusion limitation for immobilized proteins and enzymes. The method developed with immobilized HRP can also be used for biosensors with greater sensitivity in a 3D system. With an ability to detect reactants in an x, y, z coordinate system, new approaches to biosensor designs may be feasible based on this new technology.

This technique can also be used for developing gradients of other proteins, such as those required in chemotaxis (movement of cells up in a concentration gradient). The study of chemotaxis is essential to understanding cell migration in would healing, cancer metastasis and applications in tissue engineering. Traditional studies for chemotaxis still rely on a gradient of chemoattractant on two-dimensional materials, mostly slabs of PDMS (polydimethylsiloxane) or collagen and agarose gels (Li Jeon et al. 2002). Non-linear gradients developed in the 1960's by Boyden, commonly known as the Boyden chamber, are still commonly used (Boyden 1962). Recently, linear gradients made on a microfluidic device gave control over gradient concentration and linearity, thereby increasing stability of the gradient (Li Jeon et al. 2002). However, most tissues in the body are three-dimensional and cells live in a high density three dimensional environment. Chemotaxis in the body also takes place within three-dimensions, however these studies are sill predominately studied in two-dimensional environments.

Conclusion

Carbodiimide chemistry was successfully used to covalently couple HRP onto 3D silk fibroin scaffolds. A reaction pH at which minimal adsorption of HRP to silk fibroin was chosen for coupling HRP onto silk fibroin. Adsorbed HRP was only 6% of the total activity detected in the covalently immobilized HRP. Because of low HRP adsorption, it was assumed that detection of all HRP activity is an effect of covalently immobilized HRP. The diffusion method of making immobilized gradient offers increased control of gradient slopes compared to the convection method. The diffusion method described is a simple way to make protein gradients in 3D scaffolds with: changeable concentrations of covalently immobilized protein; different slopes of gradients; and the overall spread of gradient on the scaffolds. The method could also be used with other biomaterials, such as collagen foams, with different proteins, and by using a variety of coupling chemistries with different coupling kinetics. However, for uniformity of the gradient it is important that the scaffold has a consistent pore density, so that uniform and bilaterally similar gradients are generated. This method can also be translated to developing gradients from two ends of a scaffold, which can be useful for applications in tissue engineering. Covalent immobilization of HRP showed increased stability versus time compared to adsorbed HRP and increased stability versus temperature compared to both adsorbed and free HRP. Using diffusion of enzymes or growth factors into porous scaffolds to make immobilized gradients should provide new options for design features in biomaterial scaffolds and offer improved control of cell and tissue outcomes in vitro and in vivo. This control will include new aspects of regional patterning on these gradients.

EXAMPLE 2

Recombinant Human BMP-2 (rhBMP-2) Gradients

Figure 9:
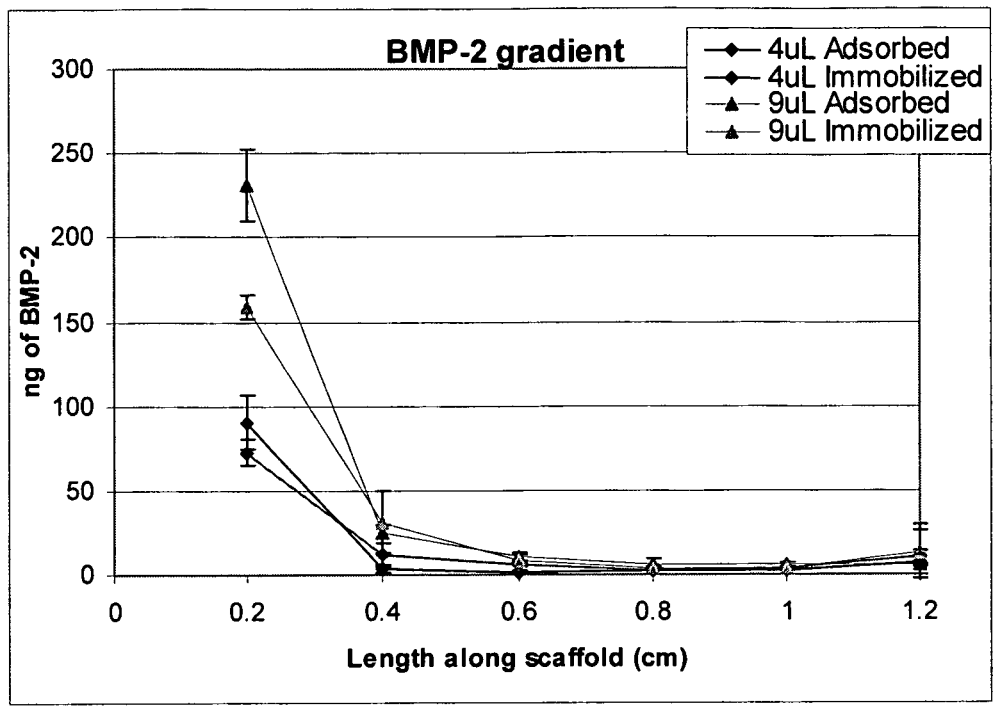
FIG. 9A shows formation of adsorbed and immobilized BMP-2 gradient with 4 μL and 9 μL volume of 0.13 mg/mL rhBMP-2 solution.
FIG. 9B shows formation of adsorbed and immobilized BMP-2 gradient with 4 μL and 9 μL volume of 0.13 mg/mL rhBMP-2 solution.
Figure 9:
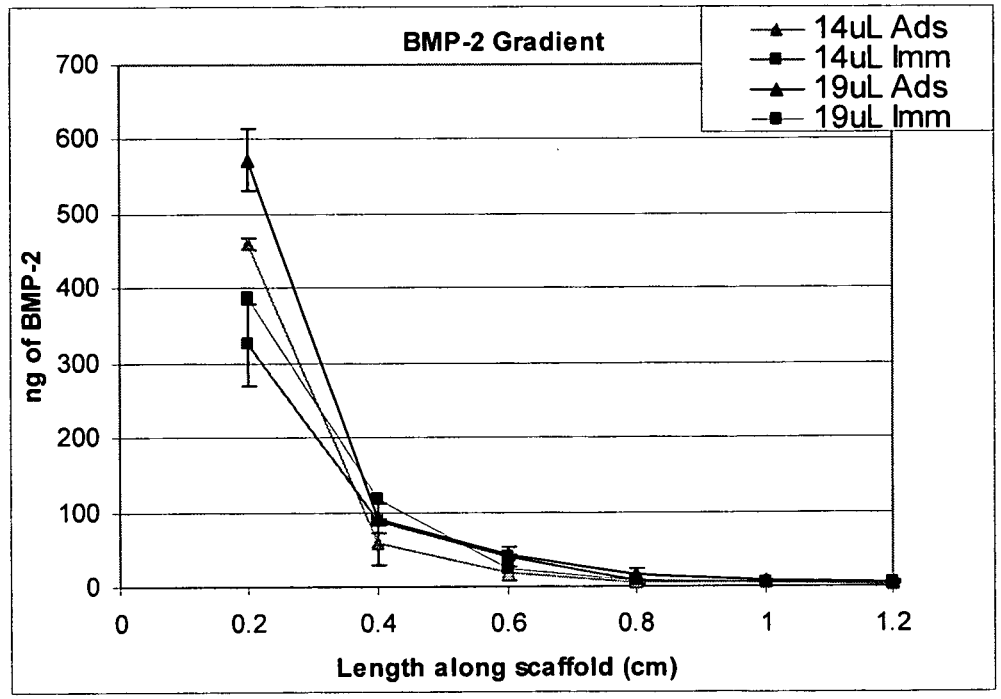

Using methods similar to Example 1 to confirm our findings with HRP, rhBMP-2 gradients were produced. Silk fibroin scaffolds were activated using EDC/NHS for 15 minutes. Different volumes of rhBMP-2 were allowed to diffuse and create different immobilized gradients of rhBMP-2 within the silk fibroin scaffold (FIGS. 9A and 9B).

Bone marrow stromal cells were seeded into the silk fibroin scaffolds and supplied with osteogenic media. Scaffolds were grown in 6 well plates for 4-5 weeks and supplied with 50 µg/ml ascorbic acid and 3 mM β-glycerophosphate and $10^{-8}$ M dexamethasone. Calcium mineral assay showed a gradient response along the length of the scaffold.

Figure 10:
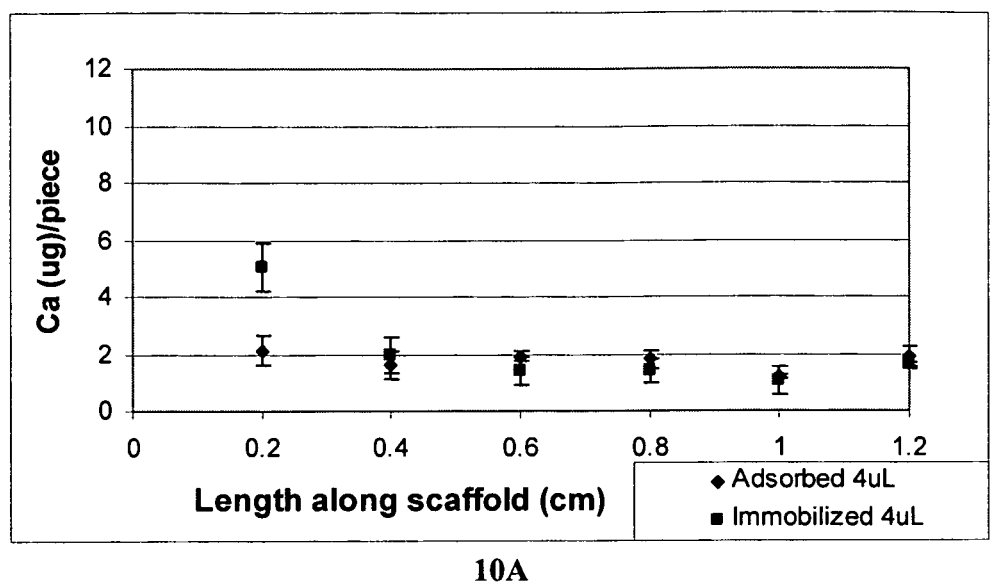
FIG. 10A shows gradient response (mineral calcium deposition by stromal cells) to 4 μL immobilized and adsorbed rhBMP-2.
FIG. 10B shows gradient response (mineral calcium deposition by stromal cells) to 19 μL immobilized and adsorbed rhBMP-2.
Figure 10:
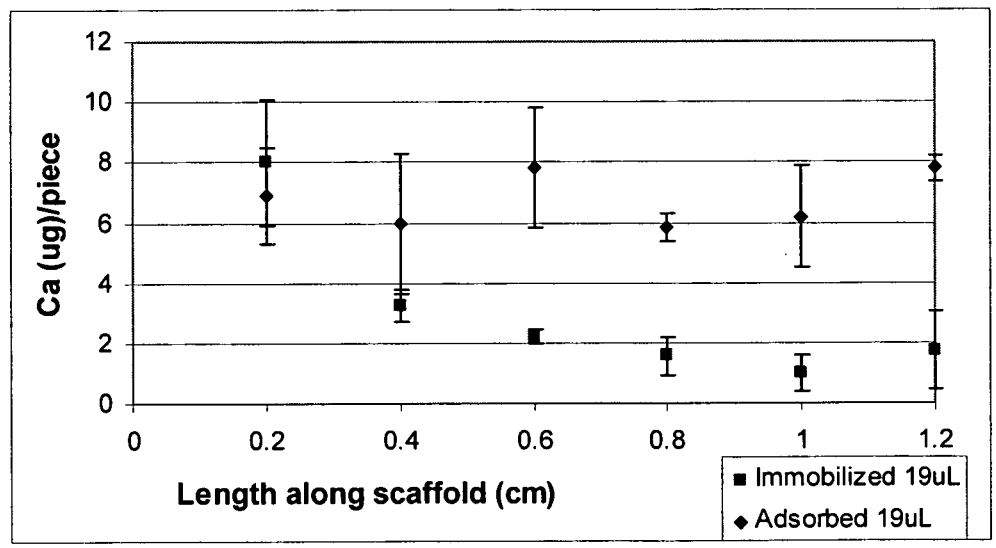
Figure 11:
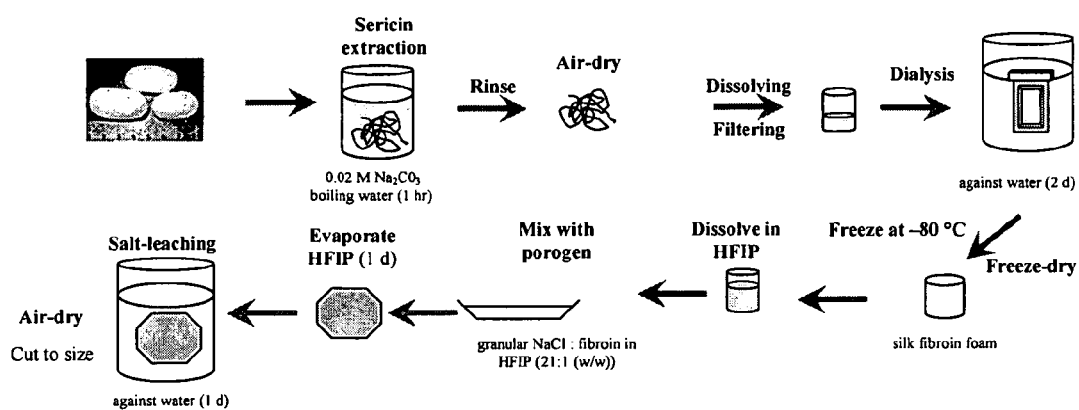
FIG. 11 is a schematic showing the preparation of silk fibroin scaffolds.

Increase in the amount of BMP-2 (from 4 µL to 9 µL), results in an increase in the calcium mineral content showing a dose dependent increase in mineral deposition with increase in BMP-2. Immobilized BMP-2 shows control in the response of human bone marrow stromal cells compared to BMP-2 that is adsorbed onto silk fibroin scaffolds (FIGS. 10A and 10B).

REFERENCES

The references cited below and throughout the specification are incorporated herein.

1. Azevedo A M, Martins, V. C., Prazeras, D. M. F., Vojinovic, V., Cabral, J. M. S., Fonseca, L. P. 2003. Horseradish peroxidase: a valuable tool in biotechnology. Biotechnology Annual Review 9:199-247.
2. Boyden S. 1962. The chemotactic effect of mixtures of antibody and antigen on polymorphonuclear leucocytes. J Exp Med 115:453-66.
3. Chen J S, Noah E M, Pallua N, Steffens G C. 2002. The use of bifunctional polyethyleneglycol derivatives for coupling of proteins to and cross-linking of collagen matrices. J Mater Sci Mater Med 13(11):1029-35.
4. Chiu D T, Jeon N L, Huang S, Kane R S, Wargo C J, Choi I S, Ingber D E, Whitesides G M. 2000. Patterned deposition of cells and proteins onto surfaces by using three-dimensional microfluidic systems. Proc Natl Acad Sci USA 97(6):2408-13.
5. Hermanson G T. 1996. Bioconjugate Techniques: Academic Press.
6. Josephy D P, Eling, T., Mason, R. P. 1982. The Horseradish Peroxidase-catalyzed Oxidation of 3,5,3',5"-Tetramethylbenzidense. Free radicals and Charge Transfer Complex Intermediates. The Journal of Biological Chemistry 257(7):3669-3675.
7. Karageorgiou V, Meinel L, Hofmann S, Malhotra A, Volloch V, Kaplan D. 2004. Bone morphogenetic protein-2 decorated silk fibroin films induce osteogenic differentiation of human bone marrow stromal cells. J Biomed Mater Res.
8. Lee C J, Huie P, Leng T, Peterman M C, Marmor M F, Blumenkranz M S, Bent S F, Fishman H A. 2002. Microcontact printing on human tissue for retinal cell transplantation. Arch Ophthalmol 120(12):1714-8.
9. Li Jeon N, Baskaran H, Dertinger S K, Whitesides G M, Van de Water L, Toner M. 2002. Neutrophil chemotaxis in linear and complex gradients of interleukin-8 formed in a microfabricated device. Nat Biotechnol 20(8):826-30.
10. McDevitt T C, Woodhouse K A, Hauschka S D, Murry C E, Stayton P S. 2003. Spatially organized layers of cardiomyocytes on biodegradable polyurethane films for myocardial repair. J Biomed Mater Res 66A(3):586-95.
11. Nazarov R, Jin H J, Kaplan D L. 2004. Porous 3-D scaffolds from regenerated silk fibroin. Biomacromolecules 5(3):718-26.
12. Olde Damink L H, Dijkstra P J, van Luyn M J, van Wachem P B, Nieuwenhuis P, Feijen J. 1996. Cross-linking of dermal sheep collagen using a water-soluble carbodiimide. Biomaterials 17(8):765-73.
13. Park S N, Lee H J, Lee K H, Suh H. 2003. Biological characterization of EDC-crosslinked collagen-hyaluronic acid matrix in dermal tissue restoration. Biomaterials 24(9):1631-41.
14. Park T H, Shuler M L. 2003. Integration of cell culture and microfabrication technology. Biotechnol Prog 19(2):243-53.
15. Pieper J S, Hafmans T, Veerkamp J H, van Kuppevelt T H. 2000. Development of tailor-made collagen-glycosaminoglycan matrices: EDCINHS crosslinking, and ultrastructural aspects. Biomaterials 21(6):581-93.
16. Puleo D A, Kissling R A, Sheu M S. 2002. A technique to immobilize bioactive proteins, including bone morphogenetic protein-4 (BMP-4), on titanium alloy. Biomaterials 23(9):2079-87.
17. Rashid M H, Siddiqui K S. 1998. Carboxy-group modification: high-temperature activation of charge-neutralized and charge-reversed beta-glucosidases from Aspergillus niger. Biotechnol Appl Biochem 27 (Pt 3):231-7.
18. Rojas-Melgarejo R, Rodríguez-López, J. P., García-Cánovas, F. and Garcia-Ruiz, P. A. 2003. Immobilization of horseradish peroxidase on cinnamic carbohydrate esters. Process Biochemistry 39(11):1455-1464.
19. Sofia S, McCarthy M B, Gronowicz G, Kaplan D L. 2001. Functionalized silk-based biomaterials for bone formation. J Biomed Mater Res 54(1): 139-48.

The invention claimed is:

1. A method for forming at least one immobilized agent gradient within a 3-dimensional porous scaffold comprising:
   (a) providing a 3-dimensional porous silk fibroin scaffold;
   (b) contacting the scaffold with an aqueous solution containing an agent to allow dispersion of the solution through at least a portion of the scaffold to form a linear gradient of the agent; and
   (c) forming a covalent link between the agent and at least the surface of pores of said scaffold, whereby a first gradient of covalently linked immobilized agent is formed in said 3-dimensional porous scaffold.

2. The method of claim 1, wherein the immobilized agent is a protein.

3. The method of claim 2, wherein the protein is an enzyme, a cytokine, a growth factor, a cell binding domain and/or other cell signaling factor.

4. The method of claim 1, wherein the immobilized agent is a chemotactic agent.

5. The method of claim 1, wherein said solution is dispersed through the scaffold by convection, diffusion or both.

6. The method of claim 1, wherein the scaffold is a hydrogel.

7. The method of claim 1, further comprising forming at least one additional agent gradient in the scaffold.

8. The method of claim 2, wherein the protein is bone morphogenetic protein (BMP).

9. A method for forming an immobilized agent gradient within a 3-dimensional porous silk fibroin scaffold comprising:
   placing a solution mixture comprising silk fibroin and a porogen in a 3-dimensional mold;
   inducing β-sheet structure in the silk fibroin to obtain a 3-dimensional aqueous-insoluble silk fibroin scaffold;
   removing the porogen to form pores within the scaffold:
   contacting the scaffold with an aqueous solution containing an agent to allow dispersion of the solution through at least a portion of the scaffold to form a linear gradient of the agent; and
   forming a covalent link between the agent and at least the surface of the pores of the scaffold, whereby a gradient of covalently linked immobilized agent is formed in the 3-dimensional porous scaffold.

10. A method for forming a cell gradient within a 3-dimensional porous scaffold comprising:
    (a) providing a 3-dimensional porous silk fibroin scaffold;
    (b) contacting the scaffold with an aqueous solution containing an agent to allow dispersion of the solution through at least a portion of the scaffold to form a linear gradient of the agent, wherein the agent is selected from the group consisting of a cytokine, a growth factor, a cell binding domain, a chemotactic agent, and a cell signaling factor; and
    (c) forming a covalent link between the agent and at least the surface of pores of the scaffold, whereby a gradient of covalently linked immobilized agent is formed in the 3-dimensional porous scaffold; and
    (d) contacting the 3-dimensional porous scaffold with cells that respond to said agent to form a cell gradient within the 3-dimensional porous scaffold.

11. The method of claim 10, wherein said agent is BMP.

12. The method of claim 1, wherein at least the surface of the pores of the scaffold is activated to allow covalent linking of the agent to the activated surface of the pores of the scaffold.

13. The method of claim 1, wherein at least the agent is activated to allow covalent linking of the activated agent to at least the surface of the pores of the scaffold.

14. The method of claim 12, wherein the at least the surface of the pores is activated using an activating agent that introduces to the surface at least one functional group selected from the group consisting of hydroxysuccinimide esters, nitro- or dinitrophenyl esters, tosylates, mesylates, triflates, disulfides, and any combinations thereof.

15. The method of claim 14, wherein the activating agent is 1-Ethyl-3-(3-dimethylaminopropyl)-carbodiimide (EDC).

16. The method of claim 13, wherein the agent is activated using an activating agent that introduces to the agent at least one functional group selected from the group consisting of hydroxysuccinimide esters, nitro- or dinitrophenyl esters, tosylates, mesylates, triflates, disulfides, and any combinations thereof.

17. The method of claim 16, wherein the activating agent is 1-Ethyl-3-(3-dimethylaminopropyl)-carbodiimide (EDC).

18. The method of claim 7, wherein the at least one additional agent gradient has a slope same as or different from the slope of the first gradient.

19. The method of claim 7, wherein the at least one additional agent gradient has a direction same as or different from the direction of the first gradient.

20. A 3-dimensional porous scaffold comprising at least one agent covalently immobilized within a biocompatible material and forming at least one linear gradient therein.

21. The 3-dimensional scaffold of claim 20, further comprising cells within the biocompatible material.

22. The 3-dimensional scaffold of claim 21, wherein the cells form a gradient response in the biocompatible material.

23. The 3-dimensional scaffold of claim 20, wherein said at least one gradient is adapted to guide cell development for tissue regeneration and repair.

24. The 3-dimensional scaffold of claim 23, wherein tissue regeneration and repair includes bone and cartilage regeneration, nerve growth, and/or angiogenesis.

25. The 3-dimensional scaffold of claim 20, further comprising a monomer or polymer within the biocompatible material.

26. The 3-dimensional scaffold of claim 25, wherein the monomer or polymer forms a polymer gradient in the biocompatible material.

27. The 3-dimensional scaffold of claim 20, wherein a first agent and a second agent are covalently immobilized within the biocompatible material such that the first agent forms a first concentration gradient in a direction opposite to a second concentration gradient formed by the second agent.

28. The 3-dimensional scaffold of claim 20, wherein the biocompatible material is selected from the group consisting of silk, collagen, keratin, fibronectin, chitosan, hyaluronic acid and alginates.

29. The 3-dimensional scaffold of claim 20, wherein the biocompatible material comprises polylactic acid, polyglycolic acid, or a combination thereof.

30. The 3-dimensional scaffold of claim 20, wherein the biocompatible material comprises silk.

31. The 3-dimensional scaffold of claim 20, wherein said at least one agent comprises a protein or peptide.

32. The 3-dimensional scaffold of claim 31, wherein the protein or peptide comprises an enzyme, a cytokine, a growth factor, a cell binding domain and/or other cell signaling factor.

33. The 3-dimensional scaffold of claim 20, wherein said at least one agent comprises an enzyme.

34. The 3-dimensional scaffold of claim 33, wherein the enzyme is selected for use as a biosensor.

35. The 3-dimensional scaffold of claim 20, wherein said at least one agent comprises a chemotactic agent.

36. The 3-dimensional scaffold of claim 20, wherein said at least one agent comprises a nucleic acid.

37. The 3-dimensional scaffold of claim 20, wherein the biocompatible material has a consistent pore density.

38. The 3-dimensional scaffold of claim 37, wherein the biocompatible material has a porosity of about 90%.

39. The 3-dimensional scaffold of claim 20, wherein surface of the biocompatible material is activated.

40. The 3-dimensional scaffold of claim 20, wherein said at least one agent is activated.

41. The 3-dimensional scaffold of claim 39, wherein the surface of the biocompatible material and/or the agent is activated using 1-Ethyl-3-(3-dimethylaminopropyl)-carbodiimide (EDC).

\* \* \* \* \*

UNITED STATES PATENT AND TRADEMARK OFFICE
CERTIFICATE OF CORRECTION

PATENT NO. : 9,290,579 B2
APPLICATION NO. : 11/407373
DATED : March 22, 2016
INVENTOR(S) : Charu Vepari et al.

It is certified that error appears in the above-identified patent and that said Letters Patent is hereby corrected as shown below:

In the Claims:

Column 13, lines 29-45, correct claim 9 from:

"A method for forming an immobilized agent gradient within a 3-dimensional porous silk fibroin scaffold comprising:
placing a solution mixture comprising silk fibroin and a porogen in a 3-dimensional mold;
inducing β-sheet structure in the silk fibroin to obtain a 3-dimensional aqueous-insoluble silk fibroin scaffold;
removing the porogen to form pores within the scaffold:
contacting the scaffold with an aqueous solution containing an agent to allow dispersion of the solution through at least a portion of the scaffold to form a linear gradient of the agent; and
forming a covalent link between the agent and at least the surface of the pores of the scaffold, whereby a gradient of covalently linked immobilized agent is formed in the 3-dimensional porous scaffold."

to read:

--A method for forming an immobilized agent gradient within a 3-dimensional porous silk fibroin scaffold comprising:
placing a solution mixture comprising silk fibroin and a porogen in a 3-dimensional mold;
inducing β-sheet structure in the silk fibroin to obtain a 3-dimensional aqueous-insoluble silk fibroin scaffold;
removing the porogen to form pores within the scaffold;
contacting the scaffold with an aqueous solution containing an agent to allow dispersion of the solution through at least a portion of the scaffold to form a linear gradient of the agent; and
forming a covalent link between the agent and at least the surface of the pores of the scaffold, whereby a gradient of covalently linked immobilized agent is formed in the 3-dimensional porous scaffold.--
In the Claims:

Signed and Sealed this
Twenty-first Day of June, 2016

Michelle K. Lee
*Director of the United States Patent and Trademark Office*

CERTIFICATE OF CORRECTION (continued)
U.S. Pat. No. 9,290,579 B2

Column 15, lines 11-12, correct claim 39 from:

"The 3-dimensional scaffold of claim 32, wherein surface of the biocompatible material is activated."

to read:

--The 3-dimensional scaffold of claim 32, wherein a surface of the biocompatible material is activated.--